United States Patent [19]  
Donald

[11] 4,054,655  
[45] Oct. 18, 1977

[54] AMINODICYANOPYRAZINES FOR CONTROLLING PLANT DISEASE

[75] Inventor: Dennis Scott Donald, Mendenhall, Pa.

[73] Assignee: E. I. Du Pont de Nemours and Company, Wilmington, Del.

[21] Appl. No.: 655,954

[22] Filed: Feb. 6, 1976

[51] Int. Cl.² .................................... A01N 9/22
[52] U.S. Cl. .......................................... 424/250
[58] Field of Search ................................ 424/250

[56] References Cited

U.S. PATENT DOCUMENTS 3,879,394   4/1975   Donald .................... 260/250 BN Primary Examiner—V. D. Turner

[57] ABSTRACT

Method of controlling plant diseases, particularly late blight and apple scab, with aminodicyanopyrazines, such as 2-t-butylamino-3-chloro-5,6-dicyanopyrazine; and agricultural compositions containing these compounds.

34 Claims, No Drawings

AMINODICYANOPYRAZINES FOR CONTROLLING PLANT DISEASE

BACKGROUND

This invention relates to aminodicyanopyrazines useful for controlling plant disease.

Some of the compounds used in this invention are claimed as novel compounds in U.S. Pat. No. 3,879,394, issued 22 Apr. 1975.

The current population explosion and concomitant world food shortage demand improvements in the efficiency of producing plants and plant products that can satisfy man's basic food needs. Protection of agricultural products from destruction by plant pathogens is one way of increasing this efficiency. This invention results from efforts to develop new agents for controlling plant disease that offer advances in both safety and efficacy.

SUMMARY

This invention includes methods of controlling a broad spectrum of plant diseases by applying a fungicidally effective amount of a compound of formula I, and suitable agricultural compositions containing such compounds.

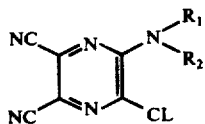

where
R$_1$ is alkyl of 2-8 carbon atoms, alkenyl of 3-8 carbon atoms, alkynyl of 3-8 carbon atoms, cycloalkylalkyl of 4-7 carbon atoms, phenyl, benzyl, α-methylbenzyl, or —NHCO$_2$R$_3$, where R$_3$ is alkyl of 1-3 carbon atoms;
R$_2$ is hydrogen, methyl, or ethyl; and
R$_1$ and R$_2$ together can be —(CH$_2$)$_n$—, wherein $n$ is 4-6.

DETAILED DESCRIPTION

Preferred Compounds

Preferred because of higher biological activity or ease of synthesis, or both, are those compounds where R$_2$ is hydrogen or methyl and R$_3$ is methyl.

More preferred are those compounds where R$_1$ is alkyl of 2-8 carbon atoms, alkenyl of 3-8 carbon atoms, alkynyl of 3-8 carbon atoms, cycloalkyl of 4-7 carbon atoms, phenyl, benzyl, or α-methylbenzyl; and R$_2$ is hydrogen or methyl.

Preferred for their disease control activity are those compounds where R$_1$ is alkyl of 2-8 carbon atoms, alkenyl of 3-8 carbon atoms, alkynyl of 3-8 carbon atoms, or cyloalkyl of 4-7 carbon atoms; and R$_2$ is hydrogen.

More preferred are those compounds where R$_1$ is alkyl of 2-6 carbon atoms, alkenyl of 3-4 carbon atoms, or alkynyl of 3-5 carbon atoms; and R$_2$ is hydrogen.

Most preferred are those compounds where R$_1$ is alkyl if 4-5 carbon atoms; and R$_2$ is hydrogen.

The following compounds specifically exemplify those that are preferred:

2-t-Butylamino-3-chloro-5,6-dicyanopyrazine, m.p. 167°–169.5° C.
2-Isobutylamino-3-chloro-5,6-dicyanopyrazine, m.p. 166°–169° C.
2-sec-Butylamino-3-chloro-5,6-dicyanopyrazine, m.p. 164°–167° C.
2-n-Hexylamino-3-chloro-5,6-dicyanopyrazine, m.p. 106°–109° C.
2-(1,1-Dimethyl-2-propnyl)amino-3-chloro-5,6-dicyanopyrazine, m.p. 129°–131° C.
2-(1.1-Dimethylpropyl)amino-3-chloro-5,6-dicyanopyrazine, m.p. 108°–111° C.
2-(2,2-Dimethylpropyl)amino-3-chloro-5,6-dicyanopyrazine, m.p. 170°–172° C.
2-(1,3-Dimethylbutyl)amino-3-chloro-5,6-dicyanopyrazine, 121°–125° C.
2-(3-Methylbutyl)amino-3-chloro-5,6-dicyanopyrazine, 114°–117.5° C.
2-(1-Ethylpropyl)amino-3-chloro-5,6-dicyanopyrazine, m.p. 132°–134° C.
2-(1-Methylbutyl)amino-3-chloro-5,6-dicyanopyrazine, m.p. 119°–121° C.

Synthesis

The process for preparing these compounds is fully disclosed in U.S. Pat. No. 3,879,394, issued 22 Apr. 1975.

Starting material, 2,3-dichloro-5,6-dicyanopyrazine, is prepared by reaction of 1,4,5,6-tetrahydro-5,6-dioxo-2,3-pyrazinedicarbonitrile with thionyl chloride.

The aminodicyanopyrazines are prepared by reaction of the starting material with the corresponding substituted amine.

The following example illustrates this process.

EXAMPLE 1

2-t-Butylamino-3-chloro-5,6-dicyanopyrazine

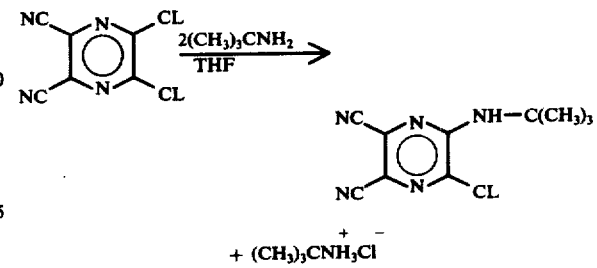

t-Butylamine, 7.3 g (.1 mole), in 50 ml of dry tetrahydrofuran was added dropwise under nitrogen to a solution of 10 g (0.05 mole) of 2,3-dichloro-5,6-dicyanopyrazine in 100 ml of tetrahydrofuran. The rate of addition was controlled so that the reactants did not exotherm to greater than 35° C. When the addition was complete, the reactants were stirred an additional half hour and then poured into 1 l. of water. After adjusting the pH to 1-2 with 10% HCl, the precipitated product was filtered and washed thoroughly with water. Crude product after drying was twice recrystallized from 1-chlorobutane to give light yellow crystals having a mp of 169°–173° C.

FORMULATION

Useful formulations of these compounds can be prepared in conventional ways. They include dusts, granules, pellets, solutions, suspensions, emulsions, wettable powders, emulsifiable concentrates and the like. Many of these may be applied directly. Sprayable formulations can be extended in suitable media and used as spray volumes of from a few to several hundred liters per hectare. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

|  | Percent by Weight | | |
| --- | --- | --- | --- |
|  | Active Ingredient | Diluent(s) | Surfactant(s) |
| Wettable Powders | 20–90 | 0–79 | 1–10 |
| Oil Suspensions, Emulsions, Solutions (including Emulsifiable Concentrates) | 5–50 | 40–95 | 0–15 |
| Aqueous Suspension Concentrates | 10–50 | 40–89 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn. Dorland Books, Caldwell, N.J. The more absorptive diluents are preferred for wettable powders and the denser ones for dusts. Typical liquid diluents and solvents are described in Marsden, "Solvents Guide," 2nd Edn., Interscience, New York, 1950. Solubility under 0.1% is preferred for suspension concentrates; solution concentrates are preferably stable against phase separation at 0° C. "McCutcheon's Detergents and Emulsifiers", McCutcheon Division, Manufacturing Confectioner Publishing Company, Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer-, pin-, or fluid energy mill. Suspensions are prepared by wet milling (see, for example, Littler, U.S. Pat. No. 3,060,084). Granules and pellets can be made by spraying the active material upon preformed granular carriers or by agglomeration techniques. See J. E. Browning, "Agglomeration", *Chemical Engineering*, Dec. 4, 1967, pp. 147ff, and "Perry's Chemical Engineer's Handbook", 4th Edn., McGraw-Hill, N.Y., 1963, pp. 8–59ff.

For further information regarding the art of formulation, see for example:

J. B. Buchanan, U.S. Pat. No. 3,576,834. Apr. 27, 1971, Col. 5 line 36 through Col. 7 Line 70 and Ex. 1–4, 17, 106, 123–140.

R. R. Shaffer, U.S. Pat. No. 3,560,616, Feb. 2, 1971, Col. 3 Line 48 through Col. 7 Line 26 and Examples 3–9, 11–18.

E. Somers, "Formulation", Chapter 6 in Torgeson, "Fungicides", Vol. I, Academic Press, New York, 1967.

In formulations containing water, such as emulsions and water suspensions, it is necessary to maintain the pH of the formulation between about 5 and 7 to insure adequate stability of the active chemical during storage. Both alkaline and acidic hydrolysis of the compounds of this invention can occur under pH conditions outside this range. A convenient method for adjusting the pH of the formulations within this range is the use of small quantities of dilute aqueous caustic or phosphoric acid solutions.

EXAMPLE 2

Wettable Powder

Eighty-two parts by weight of technical grade active chemical containing 97.6% of 2-t-butylamino-3-chloro5,6-dicyanopyrazine are thoroughly blended with 14 parts by weight of a kaolinite clay (Barden Clay, J. M. Huber Corp.) of average particle size $<1\mu$ ; 3 parts by weight of "Aerosol" OT-B, a surfactant produced by American Cyanamide Co., containing 85% by weight of the dioctyl ester of sodium sulfosuccinic acid, and one part by weight of the dispersant, hydroxypropyl-methyl cellulose (Methocel A-15, Dow Chemical Co.). The blended ingredients are hammer-milled and finally air-milled to produce a finely-divided dry powder having an average particle size of 4-5$\mu$ as determined using the Fisher Sub Sieve Sizer apparatus. The wettable powder formulation contains 80% of the active chemical and is rapidly dispersible in water.

Similar wettable powder formulations are prepared using one of the active chemicals from the following group:

a. 2-Isobutylamino-3-chloro-5,6-dicyanopyrazine;
b. 2-sec-Butylamino-3-chloro-5,6-dicyanopyrazine;
c. 2-n-Hexylamino-3-chloro-5,6-dicyanopyrazine;
d. 2-(1,1-Dimethyl-2-propynyl)amino-3-chloro-5,6-dicyanopyrazine;
e. 2-(1,1-Dimethylpropyl)amino-3-chloro-5,6-dicyanopyrazine;
f. 2-(2,2-Dimethylpropyl)amino-3-chloro-5,6-dicyanopyrazine;
g. 2-(1,3-Dimethylbutyl)amino-3-chloro-5,6-dicyanopyrazine;
h. 2-(3-Methylbutyl)amino-3-chloro-5,6-dicyanopyrazine;
i. 2-(1-Ethylpropyl)amino-3-chloro-5,6-dicyanopyrazine;
j. 2-(1-Methylbutyl)amino-3-chloro-5,6-dicyanopyrazine;

Mixtures of two or more of the active chemicals totalling 80% of the wettable powder formulation can be selected, if desired.

EXAMPLE 3

Solution

Twenty parts by weight of technical grade active chemical containing 97% by weight of 2-(methylbutyl)amino-3-chloro-5,6-dicyanopyrazine and 4 parts by weight of the surfactant Pluronic F-68 (BASF Wyandotte Corporation), a condensate of ethylene oxide with a hydrophobic base formed by condensing propylene oxide with propylene glycol, are dissolved together in 80 parts by weight of dry dimethylformamide. The resulting clear solution containing 18.7% of the active chemical is added to water to form a milky white suspension for spray applications.

Similar solution formulations are prepared using one of the active chemicals from the following group:

a. 2-t-Butylamino-3-chloro-5,6-dicyanopyrazine;
b. 2-Isobutylamino-3-chloro-5,6-dicyanopyraziine;
c. 2-sec-Butylamino-3-chloro-5,6-dicyanopyrazine;
d. 2-n-Hexylamino-3-chloro-5,6-dicyanopyrazine;
e. 2-(1,1-Dimethyl-2-propynyl)amino-3-chloro-5,6-dicyanopyrazine;
f. 2-(1,1-Dimethylpropyl)amino-3-chloro-5,6-dicyanopyrazine;
g. 2-(2,2-Dimethylpropyl)amin-3-chloro-5,6-dicyanopyrazine;
h. 2-(3-Methylbutyl)amino-3-chloro-5,6-dicyanopyrazine;
i. 2-(1-Methylbutyl)amino-3-chloro-5,6-dicyanopyrazine;
j. 2-(1-Ethylpropyl)amino-3-chloro-5,6-dicyanopyrazine;
k. 2-(1-Ethenylhexyl)amino-3-chloro-5,6-dicyanopyrazine;
l. Propyl 2-(3-chloro-5,6-dicyanopyrazine-2-yl)hydrazinecarboxylate;
m. 2-Cyclohexylmethylamino-3-chloro-5,6-dicyanopyrazine;
n. 2-(1-pyrrolidinyl)amino-3-chloro-5,6-dicyanopyrazine;
o. 2-(Hexahydroazep in-1-yl)amino-3-chloro-5,6-dicyanopyrazine;

Mixtures of two or more of the active ingredients can be selected, if desired.

EXAMPLE 4

Dust

Dust formulations containing 5% by weight of active chemical are prepared by thoroughly blending together 100 parts by weight of the wettable powder formulation of Example 2 with an additional 1500 parts by weight of the kaolinite clay. Postblending of the concentrated formulation with the diluent greatly reduces the load on milling equipment.

EXAMPLE 5

Oil Suspension

Dispersible oil supension formulations are prepared by mixing together under high shear conditions 50 parts by weight of active chemical of Example 2, 1 part by weight of calcium stearate and 149 parts by weight of a paraffinic 70 sec. SUS viscosity hydrocarbon spray oil containing an oil-in-water-emulsifier Sunspray 7E, Sun Oil Company) until viscosity of the mixture is increased to 150-200 centipoise. The resulting stable oil suspension containing 25% by weight of the active chemical is readily dispersible in water for spray applications.

EXAMPLE 6

Water Suspension

Flowable formulations which are water suspension concentrates are prepared by intensely mixing and shearing in a sand mill a mixture of 28 to 30 parts by weight of one or more of the active chemicals of Example 2, 15 parts by weight of calcium lignin sulfonate dispersant, 2 parts by weight of a montmorillonoid hydrous silicate (Fesco-Jel, F. E. Shlinder & Co.) and 0.005 parts by weight of octyl alcohol as antifoamer to produce a smooth non-settling dispersion. Several drops of 10% aqueous solution of phosphoric acid is added during milling to adjust the pH to 6. The suspension is dispersible in water to prepare spray solutions.

EXAMPLE 7

Wettable Powder

A dry mixture of 51.5 parts by weight of technical grade active chemical containing 97% by weight of 2-sec-butylamino-3-chloro-5,6-dicyanopyrazine, 32.5 parts by weight of a calcium magnesium sub-bentonite clay, Panther Creek Clay (American Colloid Co.), 5 parts by weight of the surfactant of Example 2 and one part by weight of the dispersant of Example 2 are thoroughly blended and air-milled to produce a wettable powder formulation containing 50% by weight of tee active chemical. All compounds of the invention can be formulated in a similar manner.

Use

This invention provides a method for controlling a broad spectrum of plant diseases, such as potato and tomato late blight caused by *Phytophthora infestans*, grape downy mildew caused by *Plasmopara viticola*, apple scab caused by *Venturia inaequalis*, cedar apple rust caused by *Gymnosporangium juniperi-virginianae*, wheat stem rust caused by *Puccinia graminis tritici*, bean rust caused by *Uromyces phaseoli*, and rice blast caused by *Piricularia oryzae*. This is only a representative sample of the plant diseases that can be controlled by these aminodicyanopyrazines. They are also effective against other related plant diseases.

Disease control is accomplished by applying a fungicidally effective amount of compound to the portion of the plant to be protected. These compounds also provide protection from damage caused by certain fungi when applied to the proper locus by methods described later.

Preferred rated of application for these compounds to foliage, stems, and/or fruit of living plants range from 0.05 to 20 kilogams of active ingredient per hectare. More preferred rates are in the range of 0.1 to 10 kilo grams per hectare. The most preferred rates are in the range of 0.2 to 5 kilograms per hectare. The optimum amount within this range depends upon a number of variables that are well known to those skilled in the art of plant protection. The variables include, but are not limited to, disease to be controlled, weather conditions expected, type of crop, stage of development of the crop, and interval between applications. These applications may need to be repeated one or more times at intervals of 1 to 60 days; and are made from dusts; slurries, or solutions.

Preferred rates for application to seeds, tubers, bulbs, or other plant reproductive parts range from 0.5 to 100 grams of active compound per kilogram of plantiing material treated. More preferred rates are in the range of 1 to 75 grams of active compound per kilogram. The most preferred rates are in the range of 2 to 50 grams per kilogram. These applications are made from dusts, slurries, or solutions.

Compositions of this invention may contain, in addition to the aminodicyanopyrazines, conventional insecticides, miticides, bactericids, nematicides, fungicides, or other agricultural chemical such as fruit set agents, fruit thinning compounds, fertilizer ingredients, and the like. The additional agricultural chemicals are employed in mixtures or combinations in amounts ranging from one-tenth to twenty times that of the compounds or compounds of this invention. The proper choice of amounts is readily made by one skilled in the art of protecting plants from pest depredations. The following are illustrative of the agricultural chemicals that may be included in compositions or added to sprays containing one or more of the active compounds of this invention:

bis(dimethylthiocarbamoyl)disulfide; or tetramethylthiuram disulfide (thiram);
metal salts of ethylenebisdithiocarbamic acid or propylenebisdithiocarbamic acids, e.g. manganese, zinc, iron and sodium salts (maneb or zineb);
n-dodecylguanidine acetate (dodine);
N-(trichloromethylthio)phthalimide (folpet);
N-[(trichloromethyl)thii]-4-cyclohexene-1,2-dicarboximide (captan);
cis-N-[(1,1,2,2-tetrachloroethyl)tho]-4-cyclohexene-1,2-dicarboximide (capta fol);
2,4-dichloro-6-(o-chloroanilino)-α-triazine ("Dyrene");
3,3'-ethylenebis(tetrahydro-4,6-dimethyl-2H-1,3,5-thiadiazine-2-thione), (milneb);
triphenyltin hydroxide (fentin hydroxide);
triphenyltin acetate (fentin acetate);
N'-dichlorofluoromethylthio-N,N-dimethyl-N'-phenylsulfamide (dichlorofluanid);
tetrachloroisophthalonitrile (chlorothalonil);
tribasic copper sulfate;
fixed copper;
sulfur;
methyl 1-(butylcarbamoyl)-2-benzimidazolecarbamate (benomyl);
methyl 2-benzimidazolecarbamate;
1,2-bis(3-methoxycarbonyl-2-thioureido)benzene (methyl thiophanate);
2-cyano-N-(ethylcarbamoyl)-2-methoxyiminoacetamide.

The agricultural chemicals listed above are merely exemplary of compounds that may be mixed with the active compounds of this invention to broaden the spectrum of disease control.

EXAMPLE 8

A finely ground wettable powder formulation containing 80% of the active ingredient 2-t-butylamino-3-chloro-5,6-dicyanopyrazine was suspended in water at concentrations of 75 or 300 ppm of active ingredient. The suspensions were sprayed on dwarf apple trees of the varieties Red Delicious, Golden Delicious and McIntosh on May 2, 13, and 28, June 10, 24 and July 9 and 21 (1975). Untreated trees in adjacent plantings were moderately infected with the apple scab fungus, *Venturia inaequalis*, during this period and by August 1 there were 22 scab lesions on the leaves of each terminal shoot. The trees treated with 75 ppm concentrations were almost free of disease (95 percent control) and those treated with 300 ppm were healthy and free of scab infections.

EXAMPLE 9

A finely ground wettable powder formulation (containing 80% of the active ingredient 2-t-butylamino-3-chloro-5,6-dicyanopyrazine was suspended in water at a concentration of 300 ppm of active ingredient. This suspension was sprayed to cover the foliage of field grown tomatoes on September 10, 15, 22, and 29 (1975). The untreated tomatoes in adjacent plots were severely infected with the late blight fungus, *Phytophthora infestans*, during this period and by September 30, over 96 percent of the untreated foliage and fruit were blighted. In contrast to the destruction of unprotected tomatoes, those plants treated with the compound of this invention were completely free of disease symtoms.

EXAMPLE 10

A finely ground wettable powder formulation containing 80% of the active ingredient 2-t-butylamino-3-chloro-5,6-dicyanopyrazine was suspended in water at concentrations of 16 or 80 ppm of active ingredient. The suspensions were sprayed on potted grape cuttings to the pint of run-off. After the spray deposit had dried, the grap foliage was inoculated with a spore suspension of the fungus *Plasmopara viticola* and incubated for a day in a humidity saturated chamber and then in a greenhouse for an additional week. When the untreated grape plants are incubated overnight in a humidity chamber the dorsal leaf surfaces are covered with sporulating downy mildew. In contrast, the plants treated with the compound of this invention are health — there is no evidence of downy mildew infection on those treated with 80 ppm and only an occasional lesion on the plants treated with a 16 ppm concentration.

EXAMPLE 11

Compounds of this invention were suspended at a concentration of 80 ppm in distilled water containing 300 ppm of the surfactant "Trem" 014, which consists of polyhydric alcohol esters. This suspension was sprayed to the point of run-off on tomato plants growing in pots in a greenhouse. The following day the plants were inoculated with a spore suspension of the fungus *Phytophthora infestans* and incubated in a saturated humidity at 20° C for a day and then in a greenhouse an additional four days. Disease ratings were made of each plant and this was calculated as percent control by the following formula:

$$100 - \frac{\text{disease rating on treated}}{\text{disease rating on untreated}} \times 100 = \% \text{ control.}$$

The following table shows results for some of the compounds that are effective for controlling late blight at this concentration.

| Compound | Percent Tomato late Blight Control |
|---|---|
| 2-t-Butylamino-3-chloro-5,6-dicyanopyrazine | 96 |
| 2-Isobutylamino-3-chloro-5,6-dicyanopyrazine | 88 |
| 2-(2-Methyl-2-propenyl)amino-3-chloro-5,8-dicyanopyrazine | 76 |
| 2-(1,1-Dimethyl-2-propynyl)amino-3-chloro- | 92 |

| Compound | Percent Tomato late Blight Control |
|---|---|
| 5,6-dicyanopyrazine | |
| 2-(2,2-Dimethylpropyl)amino-3-chloro-5,6-dicyanopyrazine | 72 |
| 2-sec-Butylamino-3-chloro-5,6-dicyanopyrazine | 90 |
| 2-(3-Methylbutyl)amino-3-chloro-5,6-dicyanopyrazine | 81 |
| 2-Cyclopropylmethylamino-3-chloro-5,6-dicyanopyrazine | 77 |

EXAMPLE 12

Compounds of this invention were suspended at a concentration of 80 ppm in distilled water containing 300 ppm of the surfactant "Trem" 014. This suspension was sprayed to the point of run-off on apple plants growing in pots and trained to a single shoot. The following day the apple seedlings were inoculated with a spore suspension of the fungus *Venturia inaequalis* and incubated in a saturated humidity chamber for a day, and then in a greenhouse for an additional 12 days. Disease ratings were made of each plant and this was calculated as percent control by the following formula:

$$100 - \frac{\text{disease rating on treated}}{\text{disease rating on untreated}} \times 100 = \% \text{ control}.$$

The following table shows results for some of the compounds that are effective for controlling apple scab at this concentration.

| Compound | Percent Apple Scab Control |
|---|---|
| 2-t-Butylamino-3-chloro-5,6-dicyanopyrazine | 100 |
| 2-n-Hexylamino-3-chloro-5,6-dicyanopyrazine | 98 |
| 2-Isobutylamino-3-chloro-5,6-dicyanopyrazine | 100 |
| 2-sec-Butylamino-3-chloro-5,6-dicyanopyrazine | 100 |
| 2-(1,3-Dimethylbutyl)amino-3-chloro-5,6-dicyanopyrazine | 99 |
| 2-(3-Methylbutyl)amino-3-chloro-5,6-dicyanopyrazine | 100 |
| 2-(1-Ethylpropyl)amino-3-chloro-5,6-dicyanopyrazine | 100 |
| 2-(1-Methylbutyl)amino-3-chloro-5,6-dicyanopyrazine | 99 |
| 2-(1,1-Dimethylpropyl)amino-3-chloro-5,6-dicyanopyrazine | 100 |
| 2-Ethylamino-3-chloro-5,6-dicyanopyrazine | 97 |
| 2-(2-Propenyl)amino-3-chloro-5,6-dicyanopyrazine | 89 |
| Methyl 2-(3-chloro-5,6-dicyanopyrazin-2-yl)hydrazinecarboxylate | 99 |
| 2-(1-Ethynylcyclohexylamino)-3-chloro-5,6-dicyanopyrazine | 100 |
| 2-[N-Methyl-N-(2-propynyl)]amino-3-chloro-5,6-dicyanopyrazine | 100 |
| 2-(2-Propynyl)amino-3-chloro-5,6-dicyanopyrazine | 99 |
| 2-(1-Piperidinyl)-3-chloro-5,6-dicyanopyrazine | 94 |
| 2-(N-Octyl-N-methyl)amino-3-chloro-5,6-dicyanopyrazine | 87 |
| 2-(N,N-Diethyl)amino-3-chloro-5,6-dicyanopyrazine | 98 |
| 2-(N-Phenyl-N-methyl)amino-3-chloro-5,6-dicyanopyrazine | 94 |
| 2-(α-Methylbenzyl)amino-3-chloro-5,6-dicyanopyrazine | 96 |
| 2-(N-Benzyl-N-methyl)amino-3-chloro-5,6-dicyanopyrazine | 97 |

EXAMPLE 13

2-t-Butylamino-3-chloro-5,6-dicyanopyrazine was suspended at a concentration of 100 ppm in distilled water containing 300 ppm of the surfactant "Trem" 014. This suspension was sprayed to the point of run-off on wheat and rice seedlings growing in pots in a greenhouse. The following day the wheat seedlings wer inoculated with spores of the fungus *Puccinia graminis tritici* and the rice seedlings were inoculated with spores of the fungus *Piricularia oryzae*. The inoculated seedlings were incubated for a day in a saturated humidity chamber. Disease ratings were made at a time when untreated seedlings were severely infected with numerous lesions. The wheat seedlings treated with the compounds of this invention had only an occasional rust particle and the rice was completely free of the blast disease.

I claim:
1. A composition suitable for use in controlling plant diseases caused by fungi comprising:
   a. a fungicidally effective amount of
   a compound of the formula:

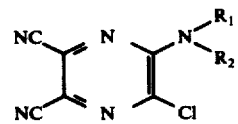

where
R₁ is alkyl of 2-8 carbon atoms, alkenyl of 3-8 carbon atoms, alkynyl of 3-8 carbon atoms, cycloalkylalkyl of 4-7 carbon atoms, phenyl, benzyl, α-methylbenzyl, or —NHCO₂R₃,
where R₃ is alkyl of 1-3 carbon atoms;
R₂ is hydrogen, methyl, or ethyl; and $R_1$ and $R_2$ together can be —$(CH_2)_n$—, where $n$ is 4–6; and b. at least one of the following: a surfactant, or a solid or liquid diluent.

2. The composition of claim 1 in which $R_2$ is hydrogen or methyl and $R_3$ methyl.

3. The composition of claim 1 in which:
$R_1$ is alkyl of 2–8 carbon atoms, alkneyl of 3–8 carbon atoms, alkynyl of 3–8 carbon atoms, cycloalkylalkyl of 4–7 carbon atoms, phenyl, benzyl, or α-methylbenzyl; and
$R_2$ is hydrogen or methyl.

4. The composition of claim 1 in which:
$R_1$ is alkyl of 2–8 carbon atoms, alkenyl of 3–8 carbon atoms, alkynyl of 3–8 carbon atoms, or cycloalkylalkyl of 4–7 carbon atoms; and
$R_2$ is hydrogen.

5. The composition of claim 1 in which:
$R_1$ is alkyl of 2–6 carbon atoms, alkenyl of 3–4 carbon atoms, or alkynyl of 3–5 carbon atoms; and
$R_2$ is hydrogen.

6. The composition of claim 1 in which:
$R_1$ is alkyl of 4–5 carbon atoms, and
$R_2$ is hydrogen.

7. The composition of claim 1 in which the active ingredient is 2-t-butylamino-3-chloro-5,6-dicyanopyrazine.

8. The composition of claim 1 in which the active ingredient is 2-isobutylamino-3-chloro-5,6-dicyanopyrazine.

9. The composition of claim 1 in which the active ingredient is 2-sec-butylamino-3-chloro-5,6-dicyanopyrazine.

10. The composition of claim 1 in which the active ingredient is 2-n-hexylamino-3-chloro-5,6-dicyanopyrazine.

11. The composition of claim 1 in which the active ingredient is 2-(1,1-dimethyl-2-propynyl)amino-3-chloro-5,6-dicyanopyrazine.

12. The composition of claim 1 in which the active ingredient is 2-(1,1-dimethylpropyl)amino-3-chloro-5,6-dicyanopyrazine.

13. The composition of claim 1 in which the active ingredient is 2-(2,2-dimethylpropyl)amino-3-chloro-5,6-dicyanopyrazine.

14. The composition of claim 1 in which the active ingredient is 2-(1,3-dimethylbutyl)amino-3-chloro-5,6-dicyanopyrazine.

15. The composition of claim 1 in which the active ingredient is 2-(3-methylbutyl)amino-3-chloro-5,6-dicyanopyrazine.

16. The composition of claim 1 in which the active ingredient is 2-(1-ethylpropyl)amino-3-chloro-5,6-dicyanopyrazine.

17. The composition of claim 1 in which the active ingredient is 2-(1-methylbutyl)amino-3-chloro-5,6-dicyanopyrazine.

18. A method of controlling plant diseases caused by fungi which comprises applying to a plant to be protected a fungicidally effective amount of a compound of the formula:

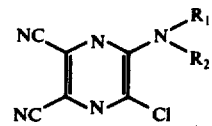

where
$R_1$ is alkyl of 2–8 carbon atoms, alkenyl of 3–8 carbon atoms, alkynyl of 3–8 carbon atoms, cycloalkylalkyl of 4–7 carbon atoms, phenyl, benzyl, α-methylbenzyl, or —$NHCO_2R_3$,
where $R_3$ is alkyl of 1–3 carbon atoms;
$R_2$ is hydrogen, methyl, or ethyl; and
$R_1$ and $R_2$ together can be —$(CH_2)_n$—, where $n$ is 4–6.

19. The method of claim 18 in which $R_2$ is hydrogen or methyl and $R_3$ is methyl.

20. The method of claim 18 in which:
$R_1$ is alkyl of 2–8 carbon atoms, alkenyl of 3–8 carbon atoms, alkynyl of 3–8 carbon atoms, cycloakylalkyl of 4–7 carbon atoms, phenyl, benzyl, or α-methylbenzyl; and
$R_2$ is hydrogen or methyl.

21. The method of claim 18 in which:
$R_1$ is alkyl of 2–8 carbon atoms, alkenyl of 3–8 carbon atoms, alkynyl of 3–8 carbon atoms, or cycloalkylalkyl of 4–7 carbon atoms; and
$R_2$ is hydrogen.

22. The method of claim 18 in which:
$R_1$ is alkyl of 2–6 carbon atoms, alkenyl of 3–4 carbon atoms, or alkynyl of 3–5 carbon atoms; and
$R_2$ is hydrogen.

23. The method of claim 18 in which:
$R_1$ is alkyl of 4–5 carbon atoms, and
$R_2$ is hydrogen.

24. The methiod of claim 18 in which the active ingredient is 2-t-butylamino-3-chloro-5,6-dicyanopyrazine.

25. The method of claim 18 in which the active ingredient is 2-isobutylamino-3-chloro-5,6-dicyanopyrazine.

26. The method of claim 18 in which the active ingredient is 2-sec-butylamino-3-chloro-5,6-dicyanopyrazine.

27. The method of claim 18 in which the active ingredient is 2-n-hexylamino-3-chloro-5,6-dicyanopyrazine.

28. The method of claim 18 in which the active ingredient is 2-(1,1-dimethyl-2-propynyl)amino-3-chloro-5,6-dicyanopyrazine.

29. The method of claim 18 in which the active ingredient is 2-(1,1-dimethylpropyl)amino-3-chloro-5,6-dicyanopyrazine.

30. The method of claim 18 in which the active ingredient is 2-(2,2-dimethylpropyl)amino-3-chloro-5,6-dicyanopyrazine.

31. The method of claim 18 in which the active ingredient is 2-(1,3-dimethylbutyl)amino-3-chloro-5,6-dicyanopyrazine.

32. The method of claim 18 in which the active ingredient is 2-(3-methylbutyl)amino-3-chloro-5,6-dicyanopyrazine.

33. The method of claim 18 in which the active ingredient is 2-(1-ethylpropyl)amino-3-chloro-5,6-dicyanopyrazine.

34. The method of claim 18 in which the active ingredient is 2-(1methylbutyl)amino-3-chloro-5,6-dicyanopyrazine.

* * * * *